United States Patent [19]
Collmer et al.

[11] Patent Number: 5,708,139
[45] Date of Patent: Jan. 13, 1998

[54] PSEUDOMONAS SYRINGAE PV SYRINGAE HRPZ GENE

[75] Inventors: Alan Collmer, Ithaca, N.Y.; Sheng-Yang He, Lexington, Ky.

[73] Assignee: Cornell Research Foundation, Inc., Ithaca, N.Y.

[21] Appl. No.: 62,024

[22] Filed: May 17, 1993

[51] Int. Cl.$^6$ .......................... C07K 14/21; C12N 15/31
[52] U.S. Cl. ..................... 530/350; 536/23.7; 435/874
[58] Field of Search .................. 530/250; 435/874; 536/23.7

[56] References Cited

U.S. PATENT DOCUMENTS

| | | | |
|---|---|---|---|
| 4,569,841 | 2/1986 | Liu | 424/93 |
| 4,597,972 | 7/1986 | Taylor | 426/36 |
| 4,601,842 | 7/1986 | Caple et al. | 252/70 |
| 4,740,593 | 4/1988 | Gonzalez et al. | 435/243 |
| 4,851,223 | 7/1989 | Sampson | 424/711 |
| 5,061,490 | 10/1991 | Paau et al. | 424/93 |
| 5,135,910 | 8/1992 | Blackburn et al. | 514/2 |
| 5,173,403 | 12/1992 | Tang | 435/6 |
| 5,217,950 | 6/1993 | Blackburn et al. | 514/2 |
| 5,243,038 | 9/1993 | Ferrari et al. | 536/23.1 |
| 5,244,658 | 9/1993 | Parke | 504/117 |
| 5,260,271 | 11/1993 | Blackburn et al. | 514/2 |

OTHER PUBLICATIONS

Stryer, "Enzymes are Highly Specific," *Biochemoistry*, San Francisco: W.H. Freeman and Company, p. 116 (1975).

Keen et al., "Inhibition of the Hypersensitive Reaction of Soybean Leaves to Incompatible Pseudomonas spp. by Blasticidin S, or Elevated Temperature," *Physiological Plant Pathology*, 18:325–337 (1981).

Lerner "Tapping the Immunological Repertoire to Produce Antibodies of Predetermined Specificity," *Nature*, 299:592–596 (1982).

Staskawicz et al., "Cloned Avirulence Gene of *Pseudomonas syringae* pv. *glycinea* Determines Race-specific Incompatibility on *Glycine max* (L.) Merr.," *Proc. Natl. Acad. Sci.*, 81:6024–6028 (1984).

Atkinson et al., "The Hypersensitive Reaction of Tobacco to *Pseudomonas syringae* pv. *pisi* $^1$," *Plant Physiol.*, 79:843–847 (1985).

Huynh et al., "Bacterial Blight of Soybean: Regulation of a Pathogen Gene Determining Host Cultivar Specificity," *Science*, 245:1374–1377 (1986).

Lindgren et al., "Gene Cluster of *Pseudomonas syringae* pv. Phaseolicola *J. Bacteriology*, Controls Pathogenicity of Bean Plants and Hypersensitivity on Nonhost Plant," 168(2):512–522 (1986).

Bauer et al., "Cloning of a Gene from *Erwinia amylovora* Involved in Induction of Hypersensitivity and Pathogenicity," *Plant Pathogenic Bacteria*, 425–429 (1987).

Collinge et al., "Plant Gene Expression in Response to Pathogens," *Plant Molecular Biology*, 9:389–410 (1987).

Shatzman et al., "Expression, Identification, and Characterization of Recombinant Gene Products in *Escherichia coli*," *Methods in Enzymology*, 152:661–673 (1987).

Shields, "towards Insect–Resistant Plants," *Nature*, 328:12–13 (1987).

Huang et al., "Molecular Cloning of a *Pseudomonas syringae* pv. *syringae* Gene Cluster That Enables *Pseudomonas fluorescens* To Elicit the Hypersensitive Response in Tobacco Plants," *Journal of Bacteriology*, 170(10):4748–4756 (1988).

Schottens–Toma et al., "Purification and Primary Structure of a Necrosis–inducing Peptide from the Apoplastic Fluids of Tomato Infected with *Cladosporium fulvum* (syn. Fulvia fulva)," *Physiological and Molecular Plant pathology*, 33:59–67 (1988).

Steinberger et al., "Creation and Complementation of Pathogenicity Mutants of *Erwinia amylovora*," *Molecular Plant–Microbe Interactions*, 1(3):135–144 (1988).

Beer et al., "The Hypersensitive Response is Elicited by *Escherichia coli* containing a cluster of Pathogenicity Genes from *Erwinia amylovora*," *Phytophathology*, 79(10):1156 (Abstract 169) (1989).

Hiatt et al., "Production of Antibodies in Transgenic Plants," *Nature*, 342:76–78 (1989).

Hippe et al., "In Situ Localization of a Foreign Protein in Transgenic Plants by Immunoelectron Microscopy Following High Pressure Freeze Substitution and Low Temperature Embedding," *European Journal of Cell Biology*, 50:230–234 (1989).

Huang et al., "Isolation and Purification of a Factor from *Pseudomonas solanacearum* That Induces a Hypersensitive–like Response in Potato Cells," *Molecular Plant–Microbe Interactions*, 2(3):132–138 (1989).

James et al., "Genetic Transformation of Apple (*Malus pumila* Mill.) Using a Disarmed Ti–binary Vector," *Plant Cell Reports*, 7:658–661 (1989).

Laby et al., "Cloning and Preliminary Characterization of an HRP Gene Cluster of *Erwinia amylovora*," *Phytopathology*, 79(10):1211 (Abstract 607) (1989).

Dow et al., "Extracellular Proteases from *Xanthomonas campestris* pv. Campestris, the Black Rot Pathogen," *Applied and Environmental Microbiology*, 56(10):2994–2998 (1990).

Walters et al., "Gene for Pathogenicity and Ability to Cause the Hypersensitive Reaction Cloned from *Erwinia amylovora*," *Physiological and Molecular Plant Pathology*, 36:509–521 (1990).

Wu et al., "Cloning, Genetic Organization, and Characterization of a Structural Gene Encoding Bacillopeptidase F from *Bacillus subtilis*," *The Journal of Biological Chemistry*, 265(12):6845–6850 (1990).

(List continued on next page.)

*Primary Examiner*—Robert A. Wax
*Assistant Examiner*—Rebecca Prouty
*Attorney, Agent, or Firm*—Nixon, Hargrave, Devans & Doyle

[57] ABSTRACT

The nucleic acid and amino acid sequences for proteinaceous elicitors of the plant defense reaction known as the hypersensitive response against *Pseudomonas syringae* are described along with method for preparation.

11 Claims, 4 Drawing Sheets

OTHER PUBLICATIONS

Bauer et al., "Further Characterization of an hrp Gene Cluster of *Erwinia amylovora*," *Molecular Plant Microbe Interactions*, 4(5):493–499 (1991).

Beer et al., "The HRP Gene Cluster of *Erwinia amylovora*," *Advances in Molecular Genetics of Plant–Microbe Interactions*, 1:53–60 (1991).

Benvenuto et al., "'Phytoantibodies': A General Vector for the Expression of Immunoglobulin Domains in Transgenic Plants," *Plant Molecular Biology*, 17:865–874 (1991).

Milat et al., "Physiological and Structural Changes in Tobacco Leaves Treated with Cryptogein, a Proteinaceous Elicitor from *Phytophthora cryptogea*," *Phytopathology*, 81(11):1364–1368 (1991).

Ruberti et al., "A Novel Class of Plant Proteins Containing a Homeodomain with a Closely Linked Leucine Zipper Motif," *The EMBO Journal*, 10(7):1787–1791 (1991).

Quigley et al., "Nucleotide Sequence and Expression of a Novel Glycine-Rich Protein Gene from *Arabidopsis thaliana*," *Plant Molecular Biology*, 17:949–952 (1991).

van Kan et al., "Cloning and Characterization of cDNA of Avirulence Gene avr9 of the Fungal Pathogen *Cladosporium fulvum*, Causal Agent of Tomato Leaf Mold," *Molecular Plant–Microbe Interactions*, 4(1):52–59 (1991).

Waldmann, "Monoclonal Antibodies in Diagnosis and Therapy," *Science*, 252:1657–1662 (1991).

Willis et al., "hrp Genes of Phytopathogenic Bacteria," *Molecular Plant–Microbe Interactions*, 4:(2) 132–138 (1991).

Beer et al., "Are Harpins Universal Elicitors of the Hypersensitive Response of Phytopathogenic Bacteria?," *Advances in Molecular Genetics of Plant–Microbe Interactions*, 2:281–286 (1992).

Laby et al., *Molecular Plant–Microbe Interactions*, 5(5):412 (1992).

Sandhu, *Crit. Rev. in Biotech.*, (92–review) 12:437–462.

Wei et al. "Harpin, Elicitor of the Hypersensitive Response Produced by the Plant Pathogen *Erwinia amylovora*," *Science*, 257:85–88 (1992).

He et al., "*Pseudomonas syringae* pv. *syringae* Harpin$_{Pss}$: A Protein that is Secreted Via the Hrp Pathway and Elicits the Hypersensitive Response in Plants," *Cell*, 73:1255–1266 (1993).

H. Huang et al. "Molecular Cloning of a *Pseudomonas syringae* pv. *syringae* Gene Cluster That Enables *Pseudomonas fluorescens* to Elicit the Hypersensitive Response in Tobacco Plants", J. Bacteriology 170(10) 4748–4756 (Oct. 1988).

Z. Wei et al., "Harpin, Elicitor of the Hypersensitive Response Produced by the Plant Pathogen *Erwinia amylovora*", Science 257: 85–88 (Jul. 1992).

S. Beer et al., "Are Harpins Universal Elicitors of the Hypersensitive Response of Phytopathogenic Bacteria" in Advances in Molecular Genetics of Plant–Microbe Interactions, Nester et al. (eds.) Kluwer Academic Publishers, Dordrecht, Netherlands pp. 281–286 (1993).

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:1:

Gly Gly Gly Leu Gly Thr Pro
              5

(2) INFORMATION FOR SEQ ID NO:2:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:2:

Gln Thr Gly Thr (2) INFORMATION FOR SEQ ID NO:3:

(i) SEQUENCE CHARACTERISTICS:
(A) LENGTH: 1400 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:3:

```
GATCCGGAAC TCGGTCGTCC AGTTCTGATT TCTTGACGCC CCTTCATACC      50

TGAGGGGGCT GCTACTTTTA GGAGGTTGTG      80

ATG CAG AGT CTC AGT CTT AAC AGC AGC TCG CTG CAA ACC     119
CCG GCA ATG GCC CTT GTC CTG GTA CGT CCT GAA GCC GAG     158
ACG ACT GGC AGT ACG TCG AGC AAG GCG CTT CAG GAA GTT     197
GTC GTG AAG CTG GCC GAG GAA CTG ATG CGC AAT GGT CAA     236
CTC GAC GAC AGC TCG CCA TTG GGA AAA CTG TTG GCC AAG     275
TCG ATG GCC GCA GAT GGC AAG GCG GGC GGC GGT ATT GAG     314
GAT GTC ATC GCT GCG CTG GAC AAG CTG ATC CAT GAA AAG     353
CTC GGT GAC AAC TTC GGC GCG TCT GCG GAC AGC GCC TCG     392
GGT ACC GGA CAG CAG GAC CTG ATG ACT CAG GTG CTC AAT     431
GGC CTG GCC AAG TCG ATG CTC GAT GAT CTT CTG ACC AAG     470
CAG GAT GGC GGG ACA AGC TTC TCC GAA GAC GAT ATG CCG     509
```

```
ATG CTG AAC AAG ATC GCG CAG TTC ATG GAT GAC AAT CCC    548

GCA CAG TTT CCC AAG CCG GAC TCG GGC TCC TGG GTG AAC    587

GAA CTC AAG GAA GAC AAC TTC CTT GAT GGC GAC GAA ACG    626

GCT GCG TTC CGT TCG GCA CTC GAC ATC ATT GGC CAG CAA    665

CTG GGT AAT CAG CAG AGT GAC GCT GGC AGT CTG GCA GGG    704

ACG GGT GGA GGT CTG GGC ACT CCG AGC AGT TTT TCC AAC    743

AAC TCG TCC GTG ATG GGT GAT CCG CTG ATC GAC GCC AAT    782

ACC GGT CCC GGT GAC AGC GGC AAT ACC CGT GGT GAA GCG    821

GGG CAA CTG ATC GGC GAG CTT ATC GAC CGT GGC CTG CAA    860

TCG GTA TTG GCC GGT GGT GGA CTG GGC ACA CCC GTA AAC    899

ACC CCG CAG ACC GGT ACG TCG GCG AAT GGC GGA CAG TCC    938

GCT CAG GAT CTT GAT CAG TTG CTG GGC GGC TTG CTG CTC    977

AAG GGC CTG GAG GCA ACG CTC AAG GAT GCC GGG CAA ACA   1016

GGC ACC GAC GTG CAG TCG AGC GCT GCG CAA ATC GCC ACC   1055

TTG CTG GTC AGT ACG CTG CTG CAA GGC ACC CGC AAT CAG   1094

GCT GCA GCC                                            1103

TGACCGACAA CCGCCTGACG GAGAACTCAC GTGACCATTT CCCACCTTGG 1153

TAATGTTAAA AGCATCTCGC CGGAACTCGG GCAGGATGTG CCACAGGGGC 1203

TCGTTTCAGA ACCGGCCCAG GCGGATGTCG ACATCTTCAC CGCTGCCACG 1253

CAGCCGGACG GCGTTTCAAG TGGAGCGCCG CTTTCCGAGC ATATCGCCAG 1303

CGCAATTTCC GGCGGTCTGG GCGAAACCGA AAAAATGTCT CAGCAAGCGA 1353

TGCGGTCGAT GAAGAAAGCC TCCGGGACTG AGACGCGCT GGATATC     1400
```

( 2 ) INFORMATION FOR SEQ ID NO:4:

( i ) SEQUENCE CHARACTERISTICS:
        ( A ) LENGTH: 1023 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:4:

```
ATG CAG AGT CTC AGT CTT AAC AGC AGC TCG CTG CAA ACC     39

CCG GCA ATG GCC CTT GTC CTG GTA CGT CCT GAA GCC GAG     78

ACG ACT GGC AGT ACG TCG AGC AAG GCG CTT CAG GAA GTT    117

GTC GTG AAG CTG GCC GAG GAA CTG ATG CGC AAT GGT CAA    156

CTC GAC GAC AGC TCG CCA TTG GGA AAA CTG TTG GCC AAG    195

TCG ATG GCC GCA GAT GGC AAG GCG GGC GGT ATT GAG        234

GAT GTC ATC GCT GCG CTG GAC AAG CTG ATC CAT GAA AAG    273

CTC GGT GAC AAC TTC GGC GCG TCT GCG GAC AGC GCC TCG    312

GGT ACC GGA CAG CAG GAC CTG ATG ACT CAG GTG CTC AAT    351

GGC CTG GCC AAG TCG ATG CTC GAT GAT CTT CTG ACC AAG    390

CAG GAT GGC GGG ACA AGC TTC TCC GAA GAC GAT ATG CCG    429

ATG CTG AAC AAG ATC GCG CAG TTC ATG GAT GAC AAT CCC    468
```

| | | | | | | | | | | | | |
|---|---|---|---|---|---|---|---|---|---|---|---|---|
|GCA|CAG|TTT|CCC|AAG|CCG|GAC|TCG|GGC|TCC|TGG|GTG|AAC|507|
|GAA|CTC|AAG|GAA|GAC|AAC|TTC|CTT|GAT|GGC|GAC|GAA|ACG|546|
|GCT|GCG|TTC|CGT|TCG|GCA|CTC|GAC|ATC|ATT|GGC|CAG|CAA|585|
|CTG|GGT|AAT|CAG|CAG|AGT|GAC|GCT|GGC|AGT|CTG|GCA|GGG|624|
|ACG|GGT|GGA|GGT|CTG|GGC|ACT|CCG|AGC|AGT|TTT|TCC|AAC|663|
|AAC|TCG|TCC|GTG|ATG|GGT|GAT|CCG|CTG|ATC|GAC|GCC|AAT|702|
|ACC|GGT|CCC|GGT|GAC|AGC|GGC|AAT|ACC|CGT|GGT|GAA|GCG|741|
|GGG|CAA|CTG|ATC|GGC|GAG|CTT|ATC|GAC|CGT|GGC|CTG|CAA|780|
|TCG|GTA|TTG|GCC|GGT|GGT|GGA|CTG|GGC|ACA|CCC|GTA|AAC|819|
|ACC|CCG|CAG|ACC|GGT|ACG|TCG|GCG|AAT|GGC|GGA|CAG|TCC|858|
|GCT|CAG|GAT|CTT|GAT|CAG|TTG|CTG|GGC|GGC|TTG|CTG|CTC|897|
|AAG|GGC|CTG|GAG|GCA|ACG|CTC|AAG|GAT|GCC|GGG|CAA|ACA|936|
|GGC|ACC|GAC|GTG|CAG|TCG|AGC|GCT|GCG|CAA|ATC|GCC|ACC|975|
|TTG|CTG|GTC|AGT|ACG|CTG|CTG|CAA|GGC|ACC|CGC|AAT|CAG|1014|
|GCT|GCA|GCC|1023|

(2) INFORMATION FOR SEQ ID NO:5:

(i) SEQUENCE CHARACTERISTICS:
        (A) LENGTH: 341 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

| | | | | | | | | | | | | | | |
|---|---|---|---|---|---|---|---|---|---|---|---|---|---|---|
|Met|Gln|Ser|Leu|Ser|Leu|Asn|Ser|Ser|Ser|Leu|Gln|Thr|Pro|Ala|
| | | | |5| | | | |10| | | | |15|
|Met|Ala|Leu|Val|Leu|Val|Arg|Pro|Glu|Ala|Glu|Thr|Thr|Gly|Ser|
| | | | |20| | | | |25| | | | |30|
|Thr|Ser|Ser|Lys|Ala|Leu|Gln|Glu|Val|Val|Lys|Leu|Ala|Glu|
| | | | |35| | | | |40| | | | |45|
|Glu|Leu|Met|Arg|Asn|Gly|Gln|Leu|Asp|Asp|Ser|Ser|Pro|Leu|Gly|
| | | | |50| | | | |55| | | | |60|
|Lys|Leu|Leu|Ala|Lys|Ser|Met|Ala|Ala|Asp|Gly|Lys|Ala|Gly|Gly|
| | | | |65| | | | |70| | | | |75|
|Gly|Ile|Glu|Asp|Val|Ile|Ala|Ala|Leu|Asp|Lys|Leu|Ile|His|Glu|
| | | | |80| | | | |85| | | | |90|
|Lys|Leu|Gly|Asp|Asn|Phe|Gly|Ala|Ser|Ala|Asp|Ser|Ala|Ser|Gly|
| | | | |95| | | | |100| | | | |105|
|Thr|Gly|Gln|Gln|Asp|Leu|Met|Thr|Gln|Val|Leu|Asn|Gly|Leu|Ala|
| | | | |110| | | | |115| | | | |120|
|Lys|Ser|Met|Leu|Asp|Asp|Leu|Leu|Thr|Lys|Gln|Asp|Gly|Gly|Thr|
| | | | |125| | | | |130| | | | |135|
|Ser|Phe|Ser|Glu|Asp|Asp|Met|Pro|Met|Leu|Asn|Lys|Ile|Ala|Gln|
| | | | |140| | | | |145| | | | |150|
|Phe|Met|Asp|Asp|Asn|Pro|Ala|Gln|Phe|Pro|Lys|Pro|Asp|Ser|Gly|
| | | | |155| | | | |160| | | | |165|
|Ser|Trp|Val|Asn|Glu|Leu|Lys|Glu|Asp|Asn|Phe|Leu|Asp|Gly|Asp|
| | | | |170| | | | |175| | | | |180|

| | | | | | | | | | | | | | |
|---|---|---|---|---|---|---|---|---|---|---|---|---|---|
|Glu|Thr|Ala|Ala|Phe<br>185|Arg|Ser|Ala|Leu|Asp<br>190|Ile|Ile|Gly|Gln|Gln<br>195|
|Leu|Gly|Asn|Gln|Gln<br>200|Ser|Asp|Ala|Gly|Ser<br>205|Leu|Ala|Gly|Thr|Gly<br>210|
|Gly|Gly|Leu|Gly|Thr<br>215|Pro|Ser|Ser|Phe|Ser<br>220|Asn|Asn|Ser|Ser|Val<br>225|
|Met|Gly|Asp|Pro|Leu<br>230|Ile|Asp|Ala|Asn|Thr<br>235|Gly|Pro|Gly|Asp|Ser<br>240|
|Gly|Asn|Thr|Arg|Gly<br>245|Glu|Ala|Gly|Gln|Leu<br>250|Ile|Gly|Glu|Leu|Ile<br>255|
|Asp|Arg|Gly|Leu|Gln<br>260|Ser|Val|Leu|Ala|Gly<br>265|Gly|Gly|Leu|Gly|Thr<br>270|
|Pro|Val|Asn|Thr|Pro<br>275|Gln|Thr|Gly|Thr|Ser<br>280|Ala|Asn|Gly|Gly|Gln<br>285|
|Ser|Ala|Gln|Asp|Leu<br>290|Asp|Gln|Leu|Leu|Gly<br>295|Gly|Leu|Leu|Leu|Lys<br>300|
|Gly|Leu|Glu|Ala|Thr<br>305|Leu|Lys|Asp|Ala|Gly<br>310|Gln|Thr|Gly|Thr|Asp<br>315|
|Val|Gln|Ser|Ser|Ala<br>320|Ala|Gln|Ile|Ala|Thr<br>325|Leu|Leu|Val|Ser|Thr<br>330|
|Leu|Leu|Gln|Gly|Thr<br>335|Arg|Asn|Gln|Ala|Ala<br>340|

( 2 ) INFORMATION FOR SEQ ID NO:6:

( i ) SEQUENCE CHARACTERISTICS:
( A ) LENGTH: 945 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:6:

```
GAT CTT CTG ACC AAG CAG GAT GGC GGG ACA AGC TTC TCC      39
GAA GAC GAT ATG CCG ATG CTG AAC AAG ATC GCG CAG TTC      78
ATG GAT GAC AAT CCC GCA CAG TTT CCC AAG CCG GAC TCG     117
GGC TCC TGG GTG AAC GAA CTC AAG GAA GAC AAC TTC CTT     156
GAT GGC GAC GAA ACG GCT GCG TTC CGT TCG GCA CTC GAC     195
ATC ATT GGC CAG CAA CTG GGT AAT CAG CAG AGT GAC GCT     234
GGC AGT CTG GCA GGG ACG GGT GGA GGT CTG GGC ACT CCG     273
AGC AGT TTT TCC AAC AAC TCG TCC GTG ATG GGT GAT CCG     312
CTG ATC GAC GCC AAT ACC GGT CCC GGT GAC AGC GGC AAT     351
ACC CGT GGT GAA GCG GGG CAA CTG ATC GGC GAG CTT ATC     390
GAC CGT GGC CTG CAA TCG GTA TTG GCC GGT GGT GGA CTG     429
GGC ACA CCC GTA AAC ACC CCG CAG ACC GGT ACG TCG GCG     468
AAT GGC GGA CAG TCC GCT CAG GAT CTT GAT CAG TTG CTG     507
GGC GGC TTG CTG CTC AAG GGC CTG GAG GCA ACG CTC AAG     546
GAT GCC GGG CAA ACA GGC ACC GAC GTG CAG TCG AGC GCT     585
GCG CAA ATC GCC ACC TTG CTG GTC AGT ACG CTG CTG CAA     624
GGC ACC CGC AAT CAG GCT GCA GCC                          648
```

-continued

| | | | | | |
|---|---|---|---|---|---|
| TGACCGACAA | CCGCCTGACG | GAGAACTCAC | GTGACCATTT | CCCACCTTGG | 698 |
| TAATGTTAAA | AGCATCTCGC | CGGAACTCGG | GCAGGATGTG | CCACAGGGGC | 748 |
| TCGTTTCAGA | ACCGGCCCAG | GCGGATGTCG | ACATCTTCAC | CGCTGCCACG | 798 |
| CAGCCGGACG | GCGTTTCAAG | TGGAGCGCCG | CTTTCCGAGC | ATATCGCCAG | 848 |
| CGCAATTTCC | GGCGGTCTGG | GCGAAACCGA | AAAAATGTCT | CAGCAAGCGA | 898 |
| TGCGGTCGAT | GAAGAAAGCC | TCCGGGACTG | GAGACGCGCT | GGATATC 945 | |

PSEUDOMONAS SYRINGAE PV SYRINGAE HRPZ GENE

Financial support for the making of the invention described herein was provided in part by a grant, No. DCB-9106431, from the National Science Foundation. Accordingly, the United States Government has certain statutory rights to this invention under 35 USC 200 et seq.

The hypersensitive response (HR) of higher plants is characterized by the rapid, localized death of plant cells at the site of pathogen invasion. It occurs during incompatible interactions, which typically involve a microorganism that causes disease only in another plant, and it is associated with resistance against many nematodes, fungi, viruses, and bacteria. The ability of bacteria to elicit HR was first reported in 1963 when Klement and coworkers injected the intercellular spaces of tobacco leaves with high levels of the fluorescent pseudomonads, *Pseudomonas syringae* pv. syringae (a pathogen of bean), *Pseudomonas syringae* pv. tabaci (a pathogen of tobacco), and *Pseudomonas fluorescens* (a nonpathogen) [see Nature 199: 299 (1963); and Phytopathology 54: 474 (1964)]. They observed that areas infiltrated with *Pseudomonas syringae* pv. syringae collapsed and desiccated within 24 hr, those infiltrated with *Pseudomonas syringae* tabaci produced slowly developing and progressively spreading watersoaked lesions, and those infiltrated with *Pseudomonas fluorescens* showed no response. At lower levels of inoculum, *Pseudomonas syringae* pv. syringae caused no visible reaction, whereas *Pseudomonas syringae* pv. tabaci again caused disease.

The species *Pseudomonas syringae* is remarkable for its pathogenic diversity (Hirano and Upper, 1990). Different strains cause symptoms ranging from galls to "wildfire" blights, well-characterized virulence (symptom enhancing) factors are as diverse as phytohormones and peptide toxins, multiple patterns of host specificity (including in some cases, avr-mediated gene-for-gene interactions) involve virtually all crop plants, and plant associations vary from epephytism to devastating pathogenesis. There is a *Pseudomonas syringae* version for many important phenomena in the interactions of plants and pathogenic microbes, and this species has accordingly attracted much investigation.

These early observations led many investigations into the study of the underlying mechanisms of HR. It is now known, for example, that a pathogen at lower concentrations in an incompatible host causes the HR in scattered, individual plant cells (with one bacterium in the leaf intercellular space triggering the death of one plant cell), and that the macroscopic HR is a manifestation of a cellular hypersensitivity that can operate under natural conditions [see Phytopathology 64:885 (1974)]. It is also known that elicitation of the HR requires a bacterium that is able to synthesize proteins and is probably in contact with the surface of the doomed plant cell [see Phytopathogenic Prokaryotes, vol. 2, Mount and Lacy, eds., Academic Press, pp 149–177 (1982)]. However, the *Pseudomonas syringae* molecule that actually elicits the HR (and paradoxically, also appears essential for pathogenesis) has remained elusive.

The ability of *Pseudomonas syringae* strains to elicit the HR or pathogenesis in nonhost or host plants, respectively, is controlled by hrp genes, and typical Hrp mutants have the null phenotype of a nonpathogen in all plants [see Proc. Natl. Acad. Sci. USA 82:406 (1985); J. Bacteriol. 168:512 (1986); and Mol. Plant-Microbe Interact. 4:132 (1991)]. hrp genes are clustered, and some appear to be widely conserved in Gram-negative bacterial pathogens that cause eventual necrosis in their hosts. These pathogens include *Pseudomonas syringae, Pseudomonas solanacearum, Xanthomonas campestris, Erwinia amylovora, Erwinia stewartii,* and *Erwinia chrysanthemi* [see Mol. Plant-Microbe Interact. 5:390 (1992)]. The hrp clusters from *Pseudomonas syringae* pv syringae 61 (which has been deposited with the American Type Culture Collection under the provisions of the Budapest Treaty and which is designated as ATCC 55427) and *Erwinia amylovora* Ra321 are unique in that they enable nonpathogenic bacteria to elicit the HR in tobacco and other plants [see J. Bacteriol. 170:4748 ((1988); and Advances in Molecular Genetics of Plant-Microbe Interactions, vol. 2, Nester and Verma, eds., Kluwer Academic Publishers, pp 53–60 (1991)]. Thus, a 25-kb cluster of *Pseudomonas syringae* pv syringae 61 hrp genes is sufficient for the HR phenotype (but not the pathogenic phenotype) of the bacterium [see J. Bacteriol. 170:4748 (1988)].

Early research leading to the present invention involving TnphoA mutagenesis and complementation analysis of the HR-active cluster of *Pseudomonas syringae* pv syringae 61 hrp genes carried on cosmid pHIRII enabled us to initially identify 13 complementation groups at the cistron level, including two that encode envelope proteins [see Mol. Plant-Microbe Interact. 4:469 (1991), the disclosure of which is incorporated in toto herein]. All of the TnphoA mutations in complementation groups II through XIII have strong Hrp phenotypes, including loss of the ability to multiply or cause disease in bean plants and to elicit the HR in tobacco cells. DNA sequence analysis of the two genes encoding envelope proteins revealed that the hepH (group X) product is similar to outer membrane proteins involved in protein or phage secretion in many Gram-negative bacteria, and Hrpl (group IV) is a member of a superfamily of inner membrane proteins with an apparent function in protein secretion regulation [see J. Bacteriol. 174:4338 (1992); and J. Bacteriol. 174:6878 (1992]. Putative open reading frames for these proteins have also been reported in *Pseudomonas solanacearum* and *X. campestris* pv vesicatoria, and *Erwinia amylovora* has been shown also to produce a Hrpl protein [see Mol. Plant-Microbe Interact. 5:390 (1992); and Mol. Plant-Microbe Interact. 5:384 (1992)]. These observations support the hypothesis that some of the conserved hrp genes are involved in the secretion of one or more proteins that elicit the HR in nonhosts and are required for pathogenesis in hosts. A protein elicitor of the HR, named harpin, has been isolated from *Erwinia amylovora* Ea321, the fire blight pathogen of rosaceous plants [see Science 257:85 (1992), the disclosure of which is incorporated in toto herein]. Harpin is a heat-stable, cell envelope-associated protein with an apparent molecular mass of 44 kDa. Mutants deficient in the cognate hrpN gene are unable to elicit the HR in tobacco leaves or to produce symptoms in highly susceptible, mature pear fruit.

Identification of the *Pseudomonas syringae* HR elicitor would be particularly useful, because this species and its many pathovars have become a model for investigating several key phenomena in plant-pathogen interactions. Unfortunately, attempts to use the *Erwinia amylovora* hrpN gene and antibodies to its product failed to reveal a corresponding *Pseudomonas syringae* pv syringae elicitor; no hrpN homolog by low stringency probing of Southern blotted *Pseudomonas syringae* pv syringae 61 hrp DNA and no cross-reactive proteins in immunoblots of proteins from bacteria actively expressing the *Pseudomonas syringae* pv syringae 61 hrp genes we able to be located by these methods, and it was also not possible to detect elicitor activity in cell-free extracts or culture fluids of bacteria expressing these hrp genes. Nevertheless, the observation that HrpH is required for the HR suggested that the *Pseudomonas syringae* pv syringae 61 HR elicitor is also a secreted protein, albeit a protein that is dissimilar in primary structure and more elusive than the *Erwinia amylovora* harpin, To find such a protein we developed an in situ lysis procedure, one aspect of the present invention, that enabled us to directly screen an expression library of *Pseudomonas syringae* pv syringae 61 harpin genes for HR eliciting activity.

Thus, the hrp genes are the common denominator underlying the pathogenic diversity of *Pseudomonas syringae*, and the elucidation of hrp gene functions in this species could have broad explanatory power. We have discovered and describe herein that the biologically active product of the *Pseudomonas syringae* pv syringae 61 hrp cluster is an extracellular 34.7 kDa protein, harpin$_{Pss}$. Harpin$_{Pss}$ is secreted to the extracellular milieu in a hrp-dependent manner and is the first protein clearly demonstrated to reach the extracellular milieu via the recently discovered Hrp secretion pathway.

Utilizing the in situ lysing technique, we are now able to describe another aspect of the present invention, specifically that complementation group XII in the *Pseudomonas syringae* pv syringae 61 hrp cluster encodes a 34.7 kDa protein that is secreted in a hrpH-dependent, elicits the HR in tobacco leaves, and possesses elicitor information in a carboxyl-terminal region with repeated amino acid sequences. The protein designated harpin$_{Pss}$, is dissimilar in its amino-acid sequence to the *Erwinia amylovora* harpin$_{Ea}$, but the two harpins are similar in several other properties that predict common structural features of a class of proteins with HR-eliciting activity. We used Southern blot analysis to determine that a homolog of the harpin$_{Pss}$-encoding hrpZ gene is present in several important strains in different pathovars of *Pseudomonas syringae*. Finally, metabolic inhibitors ($\alpha$-amanitin, cycloheximide, sodium vanadate and lithium chloride (Sigma Chemical Co.)) were used to demonstrate that the HR elicited by harpin$_{Pss}$ in tobacco results from an active response of the plant. Pathogenicity, parasitic compatibility, hypersensitivity, and host range determination are central phenomena in plant-microbe interactions that are particularly approachable with the *Pseudomonas syringae* pathogens. The discovery of a molecule that mediates essential interactions of *Pseudomonas syringae* with plants should accelerate molecular explanation of these phenomena.

These and other aspects of the present invention will become more apparent with regard to the following figures, examples and detailed description of the present invention.

In the figures.

Figure 5:
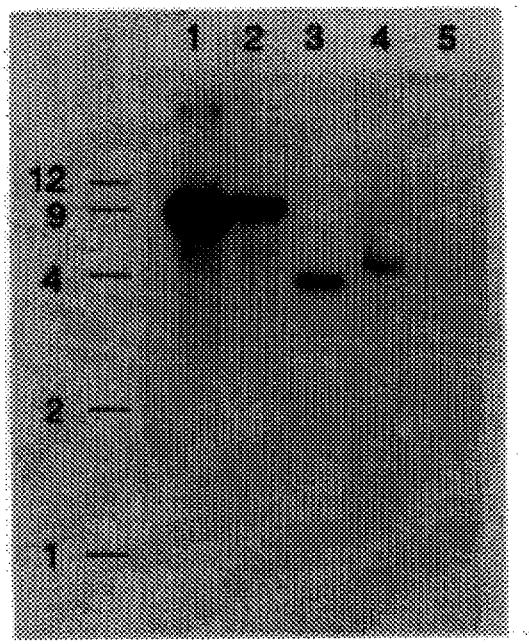
Figure 6:
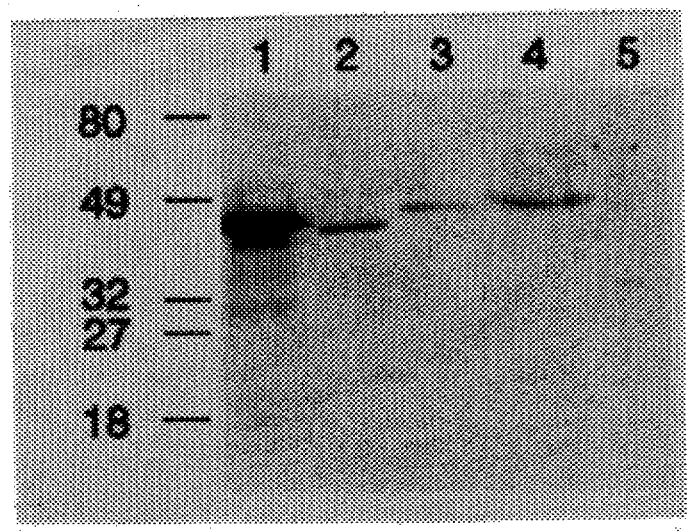

FIG. 5 provides Southern blot evidence that three strains of *Pseudomonas syringae* according to the present invention carry a hrpZ homolog; and FIG. 6 depicts immunoblot showings for harpin$_{Pss}$ homologs in three additional strains of *Pseudomonas syringae*.

Figure 1:
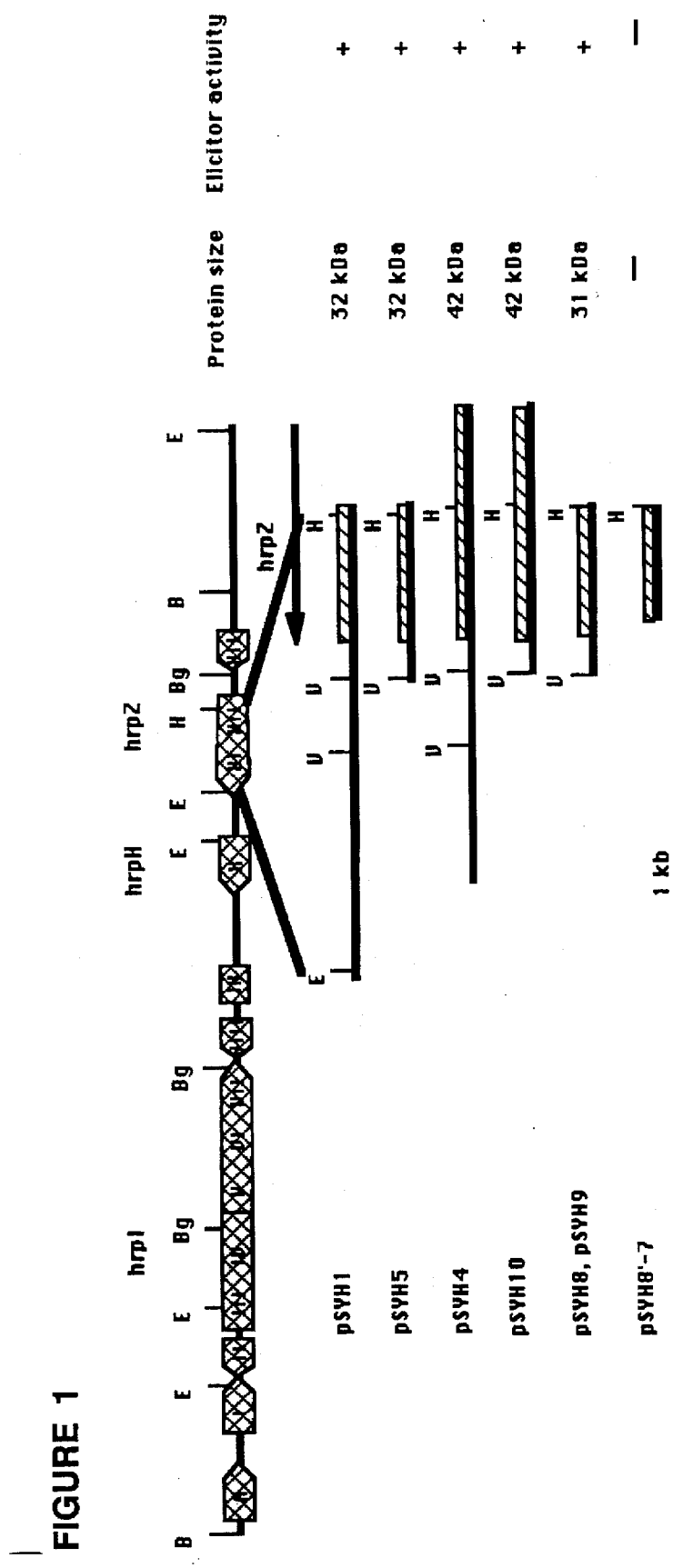
FIG. 1 depicts a restriction map of pHIR11 subclones producing an HR elicitor according to the present invention.

More specifically, FIG. 1 contains a top line indicating pHIR11 and complementation groups (determined by TnphoA mutagenesis) and putative transcription units (determined by Tn-gusA1 mutagenesis and DNA sequence analysis) that comprise the hrp cluster [see Mol. Plant-Microbe Interact. 4:469 (1991); Huang et al., Characterization of the *Pseudomonas syringae* pv. syringae hrpJ and hrpI genes:homology of HrpI to a superfamily of proteins associated with protein translocation, Mol. Plant-Microbe Interact. in press (1993); and J. Bacteriol. 174:1734 (1992)]. The two genes encoding secretion-related envelope proteins (hrpI and hrpH) and the elicitor gene (designated hrpZ) are identified. The complementation group A (hrmA) is not required for pathogenesis, and the complementation groups A, I, and II have been defined by both TnphoA and Tn-gusA1 insertions [see see Mol. Plant-Microbe Interact. 4:469 (1991); Huang et al., Characterization of the *Pseudomonas syringae* pv. syringae hrpJ and hrpI genes:homology of HrpI to a superfamily of proteins associated with protein translocation, Mol. Plant-Microbe Interact. in press (1993); and J. Bacteriol. 174:1734 (1992)]. pSYH1 and pSYH4 were identified in a random library of pHIR11 subclones by their HR-eliciting activity in tobacco leaves. Subclones pSYH5 and pSYH8 are derivatives of pSYH1; all others are from pSYH4. The products of these subclones were analyzed on SDS-PAGE gels and indicate that the 32-kDa protein is a derivative of the 42-kDa protein with a truncated amino terminus. The hatched boxes denote the extent of the hrpZ open reading frame present in each subclone; B refers to BamHI; Bg refers to BflII; E refers to EcoRI; H refers to HindIII; and V refers to EcoRV.

With regard to FIG. 2, the subclones and deletion derivatives of hrpZ were constructed in pBluescript by exploiting the restriction sites (shown in the top line in the figure and in the DNA sequence depicted below) as described in the following examples. Open bars depict the HrpZ product of each plasmid, with the amino terminus at the left. pSYH10 carries the complete hrpZ open reading frame, and has been deposited as *E. coli* DH5α(pSYH10) with the American Type Culture Collection in accordance with Budapest Treaty provisions. The deposit number is ATCC 69317. The solid bar denotes the 22 amino acid region showing similarity with harpin$_{Ea}$ (see the DNA sequence depicted below). The hatched bars denote the GGGLGTP direct repeats; the stippled bars denote the QTGT direct repeats. PMSF-treated soluble extracts of sonicated *E. coli* DH5α transformants were assayed for their ability to elicit a typical HR in tobacco leaves following the procedure outlined in Beer [see Science 257:85 (1992)] wherein "+" depicts the HR, and "−" depicts no response observed.

Figure 3:
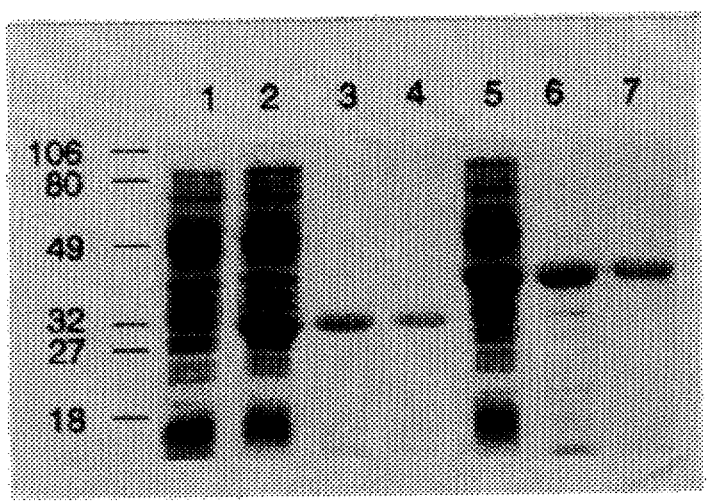
FIG. 3 depicts the SDS-PAGE analysis of Harpin$_{Pss}$ and Harpin$_{Pss}$Δ125 proteins produced by *E. coil* transformants before and after purification according to the present invention.

With regard to FIG. 3, an SDS-12% PAGE gel prepared using conventional techniques and stained with coomassie blue, shows the partial purification resulting from heat treatment of crude elicitor preparations according to the present invention and the further purification resulting from electrophoresis through 4% NuSeive agarose (FMC) and subsequent electroelution. Lanes 1, 2 and 5 shows total protein extracts from *E. coli* DH5α(pBluescript), DH5α (pSYH1) and DH5α(pSYH4), respectively; 3 and 6 shows soluble proteins in heat-treated sonicates from DH5α (pSYH1) and DH5α(pSYH4); 4 shows gel-purified harpin$_{Pss}$Δ125 from DH5α(pSYH1); and 7 indicates gel-purified harpin$_{Pss}$ from DH5α(pSYH4). The molecular masses (kDa) of commercial standard marker proteins are shown at the left.

Figure 4A:
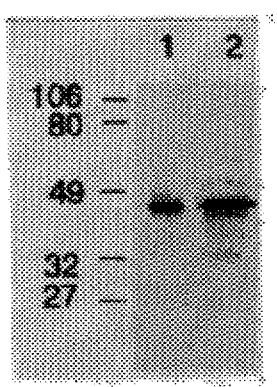
FIGS. 4A, 4B and 4C depict immunoblots showing the equivalence of the Harpin$_{Pss}$ proteins produced by *E. coli* (pSYH4) and *Pseudomonas syringae* pv syringae 61 and the hrpH-dependent secretion of harpin$_{Pss}$ in 61 cultures grown in minimal media according to the present invention.
Figure 4B:
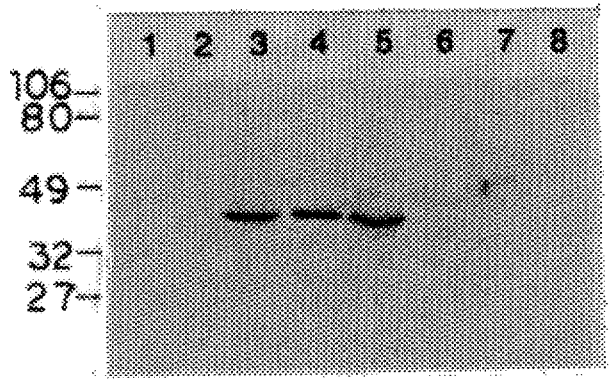
Figure 4C:
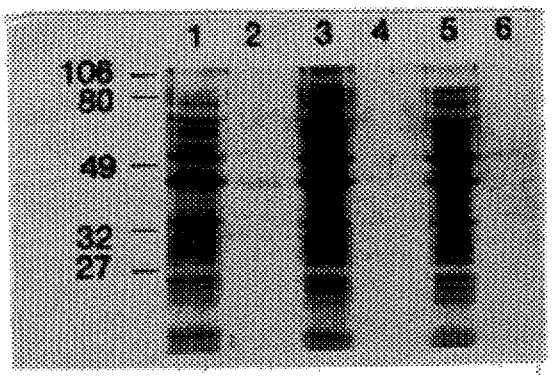

With regard to FIGS. 4A, 4B and 4C, bacteria were grown in King's B medium to an $OD_{600}$ of 0.5 to 0.8, and then incubated for 24 hours in either minimal medium or in King's B as described in more detail in Example III. The cell and extracellular fractions were then separated by centrifugation and boiled in SDS loading buffer before proteins were resolved by electrophoresis through a 10% polyacrylamide gel and either immunoblotted and proved with anti-harpin$_{Pss}$ antibodies (A and B) or stained with coomassie blue (C). The molecular masses (kDa) of marker proteins are shown at the left of each figure.

More specifically, FIG. 4A depicts an immunoblot probed with anti-harpin$_{Pss}$ antibodies and visualized with goat anti-rabbit antibody conjugated with alkaline phosphatase, showing identical mobilities of the harpin$_{Pss}$ proteins produced by *E. coli* DH5α(pSYH4) and *Pseudomonas syringae* pv syringae 61. Lane 1 shows purified harpin$_{Pss}$ from *E. coli* DH5α(pSYH4); 2 shows lysates of *Pseudomonas syringae* pv syringae 61 cells grown in minimal media. More specifically, FIG. 4B depicts an immunoblot showing that the production of extracellular harpin$_{Pss}$ in *Pseudomonas syringae* pv syringae is dependent upon hrpH, hrpZ, and hrp-derepressing minimal medium. Lane 1 shows the cell fraction from strain 61 in King's B medium; 2 shows the extracellular fraction from strain 61 in King's B medium; 3 shows the cell fraction from strain 61 in minimal media; 4 shows the extracellular fraction from strain 61 in minimal medium; 6 shows the extracellular fraction from 61-2089 in minimal medium; 7 shows the cell fraction from hrpZ mutant 61-2092 in minimal medium; and 8 shows the extracellular fraction from 61-2092 in minimal medium. More specifically, FIG. 4C depicts the coomassie-stained SDS-PAGE gel of the same samples that were analyzed in lanes 3–8 shown in FIG. 4B. Lanes 1 through 6 are in register with lanes 3 through 8 above, and show that the secretion of harpin$_{Pss}$ to the extracellular fraction is not a result of cell lysis.

More specifically, the Southern blot depicted in FIG. 5 shows the hybridization of a hrpZ probe with EcoR1 fragments in pHIR11 (lane 1), and in the genomic DNA of *Pseudomonas syringae* pv syringae B728a (lane 2). *Pseudomonas syringae* pv glycinea race 4 (lane 3), and *Pseudomonas syringae* pv tomato DC3000 (lane 4). Similarly digested DNA of *X. campestris* glycines (lane 5) failed to hybridize. The probe used in collecting this data was the 0.75 kb BstX1 internal fragment of the hrpZ gene shown in the sequence below, labelled with $^{32}$P-dCTP using Prime-it II (Statagene) following the manufacturer's instructions. Hybridization was performed with the Immobilon-N membrane (Millipore) at moderate temperatures of 58°–60° C. for 14 hours. The membrane was then washed in 2× SSC containing 0.1% SDS for 15 minutes at room temperature, followed by an additional wash in 0.1× SSC containing 0.5% SDS for 1 hour at 58°–60° C. Autoradiography was done at −80° C. for 3 hr (lanes 1, 2, 3, 5) and 7 hr (lane 4) using Kodak X-Omat AR films. The size of standard marker fragments are shown at the left.

With specific regard to FIG. 6, there is seen immunoblots prepared from other *Pseudomonas syringae* strains. To obtain these immunoblots, cultures were grown for 24 hr in minimal medium and sonicated directly in the culture medium. Proteins were resolved by SDS-10% PAGE and immunostained as in FIG. 4A. Lane 1 shows *Pseudomonas syringae* pv syringae 61; 2 shows *Pseudomonas syringae* pv syringae B728a; 3 shows *Pseudomonas syringae* pv glycinea race 4; 4 shows *Pseudomonas syringae* pv tomato DC3000; 5 shows *Pseudomonas fluorescens* 55. The molecular masses (kDa) of standard marker proteins are shown at the left.

In the following description, plants of commercially available species of tobacco (*Nicotiana tabacum* L. cv. Samsun), tomato (*Lycopersicon esculentum* Mill. cv. Pearson), soybean (*Glycine max* L. cv. Norchief), potato (Solanum tuperosum L. cv. Katahdin), and bean (*Phaseolus vulgaris* L. cv. Pinto) were grown in a greenhouse at 23°–25° C. with a photoperiod of 16 hours. *A. thaliana* (Co-1) plants were grown at 21°–23° C. with a photoperiod of 16–24 hours.

The laboratory technique used in the following description of the present invention to demonstrate the HR is straight-forward. The intercellular spaces of tobacco leaves are infiltrated by first puncturing a sector on a leaf with a common straight dissecting needle. Then a 1-ml capacity syringe (without a needle), containing 0.1–0.5 ml of a bacterial cell suspension (usually $10^7$–$10^8$ viable cells/ml) of bacteria is pressed against one side of the leaf directly over the puncture. While pressing a finger on the opposite side of the leaf to stabilize it and to prevent liquid from leaking out of the punctured area, the syringe plunger is pressed gently to introduce the bacterial suspension into the leaf. Infiltration is considered successful when a water-soaked area approximately 1–4 cm$^2$ appears in the leaf. Infiltration of plant leaves with harpin$_{Pss}$ preparations (in 5 mM phosphate buffer, pH 6.5) or bacteria (in 10 mM MgCl2) is described below.

All DNA manipulations described herein, except when specified, followed conventional protocols [see Ausubel, et.al., Current protocols in molecular biology, John Wiley (1987); and Sambrook, supra]. DNA sequencing was performed using the Sequenase Version 2.0 kit (U.S. Biochemical). Sequences were analyzed with the Genetics Computer Group Sequence Analysis Software package [see Gene 12:387 (1984)].

The two *Pseudomonas syringae* pv syringae TnphoA mutants used, 61-2089 and 61-2092, were constructed previously [see Mol. Plant-Microbe Interact. 4:469 (1991)]; the *Pseudomonas syringae* pv glycinea race 4 (a pathogen on some cultivars of soybean), *Pseudomonas syringae* pv tomato strain DC3000 (a pathogen on some cultivars of tomato), as well as *A. thaliana* were obtained from various sources; and *Pseudomonas fluorescens* 55 (a nonpathogen) has been previously reported [see J. Bacteriol. 170:4748 (1988)]. The *E. coli* strain used primarily was DH5α (Bethesda Research Laboratories) [see J. Mol. Biol. 166:557 (1988)]; and MC4100 [see Silhavy et al., Experiments with gene fusions, Cold Spring Harbor (1984)] were used in those experiments where the Hrp+ phenotype of pHIR11 needed to be observed. pHIR11 a cosmid clone containing a 25-kb, hrp gene cluster of *Pseudomonas syringae* pv syringae 61 and enables nonpathogenic bacteria, such as *Pseudomonas fluorescens* and many RecA$^+$ strains of *E. coli*, to elicit the hypersensitive response in plants [see J. Bacteriol. 170:4748 (1988)]. pSYH1 and pSYH4 are subclones of pHIR11 in pBluescript SK (Statagene) containing the hrpZ gene of *Pseudomonas syringae* pv syringae.

The microorganisms described herein, whether used for making of the present invention or as screens to demonstrate utility, were obtained from commercial sources, from the authors of previous publications cited herein, or have been deposited with the American Type Culture Collection (Bethesda, Md.). In addition, the microorganisms described herein are maintained in the Department of Plant Pathology at Cornell University (Ithaca, N.Y.) and will be maintained and made available to investigators requesting the same from the Department of Plant Pathology under provisions equivalent to the Budapest Treaty.

Pseudomonads were routinely grown in King's B broth [see J. Lab. Med. 22:301 (1954)] at 30° C. unless the cultures specify the hrp-derepressing minimal medium of Huynh [see Science 245:1374 (1989)], adjusted to pH 5.5. *E. coli* was grown in LM or Terrific Broth [see Sambrook et al., Molecular Cloning:A Laboratory Manual, 2nd ed., Cold Spring Harbor Laboratory (1989)] at 37° C. for plasmid extraction and at 30° C. for protein expression. Plasmids were introduced into bacteria by chemical transformation following recognized techniques reported by Sambrook, supra, or electroporation using a Gene Pulsar (Bio-Rad) according to the manufacturer's directions.

A rapid procedure for identifying harpin$_{Pss}$-producing recombinant *E. coli* based on in planta bacterial lysis is described in the following example.

EXAMPLE I

Partial Sau3A subclones of pHIR11 (inserts of 1.5–3.5 kb were established in pBluescript SK(−) and maintained in *E. coli* DH5α using conventional techniques. 200 randomly chosen transformants were screened for HR-eliciting activity in tobacco leaves. Transformants were grown with constant shaking in Terrific Broth with 1 mM IPTG at room temperature. Bacteria were harvested by centrifugation and incubated for 10 min in a solution consisting of 50 mM glucose, 25 mM Tris-HCl (pH 8.0), and 10 mM EDTA at an $OD_{600}$ of 0.4 to 0.6. This treatment rendered the bacterial outer membrane permeable to macromolecules such as lysozyme which lyses bacteria. Cells were then collected by centrifugation and resuspended in the same volume of 10 mM Tris-HCl (pH 8.0) containing 2 mg/ml lysozyme. The suspension was immediately infiltrated into tobacco leaves. The HR phenotype was recorded 24 hours later.

Harpin$_{Pss}$, according to the present invention, was purified to homogeneity using the following example.

EXAMPLE II

*E. coli* DH5α cells containing appropriate plasmids were grown in Terrific Broth at 30° C. overnight in the presence of 1 mM IPTG. Bacteria were harvested by centrifugation, the pellet washed once in 10 mM phosphate buffer (pH 6.5), and resuspended in one-tenth volume of the same buffer supplemented with 1 mM phenylmethylsulfonyl fluoride (PMSF, a serine protease inhibitor). The cells were then disrupted by sonication using a Sonicator Ultrasonic Cell Disruptor™ (Heat System-Ultrasonics) at a power output of 4, and the pulsar cycle timer set to 40% duty cycle (under these conditions, 10 ml of bacterial suspension were sonicated for 10 min on ice). The sonicate was incubated at 100° C. for 10 min, followed by centrifugation at 16,500× g for 20 min. Proteins in the supernatant were separated by conventional horizontal agarose gel electrophoresis in a buffer consisting of 0.025M Tris, 0.192M glycine, pH 8.3. Agarose regions containing individual proteins were excised, and the proteins were eluted from the excised blocks of Agarose using an Elutrap apparatus (Schleicher and Schuell) following the manufacturer's directions. The eluate was desalted by passage through Sephadex G-25 spin columns. Conditions for SDS-polyacrylamide gel electrophoresis and immunoblotting were the same as reported by He [see J. Bacteriol. 173:4310 (1991)].

The detection of elicitor activity in the extracellular fluids of cultures *Pseudomonas syringae* pv syringae was conducted as described in the following example.

EXAMPLE III

*Pseudomonas syringae* pv syringae strains 61 and 61-2089 were first grown in 50 ml King's B broth at 30° C. to an $OD_{600}$ of 0.5 to 0.8. Cells were collected by centrifugation, washed once in 5 ml of hrp-derepressing minimal medium [see Science 245:1374 (1989)], resuspended in 50 ml of the same medium, and incubated, with shaking, overnight. The cultures were centrifuged at 27,000×g for 30 min and the resulting supernatants were immediately put into a boiling water bath for 10 min, dialyzed against 200 volumes of 10 mM MES (pH 5.5) and 1 mM PMSF overnight, and concentrated 50-fold by ultrafiltration with Centricon 10 tubes (Amicon). The concentrated supernatants were then diluted to various degrees with the same buffer and infiltrated into tobacco leaves. HR symptoms were recorded 24 hours later.

The construction and analysis of hrpZ derivatives according to the present invention producing truncated harpin$_{Pss}$ polypeptides was conducted according to the following example.

Figure 2:
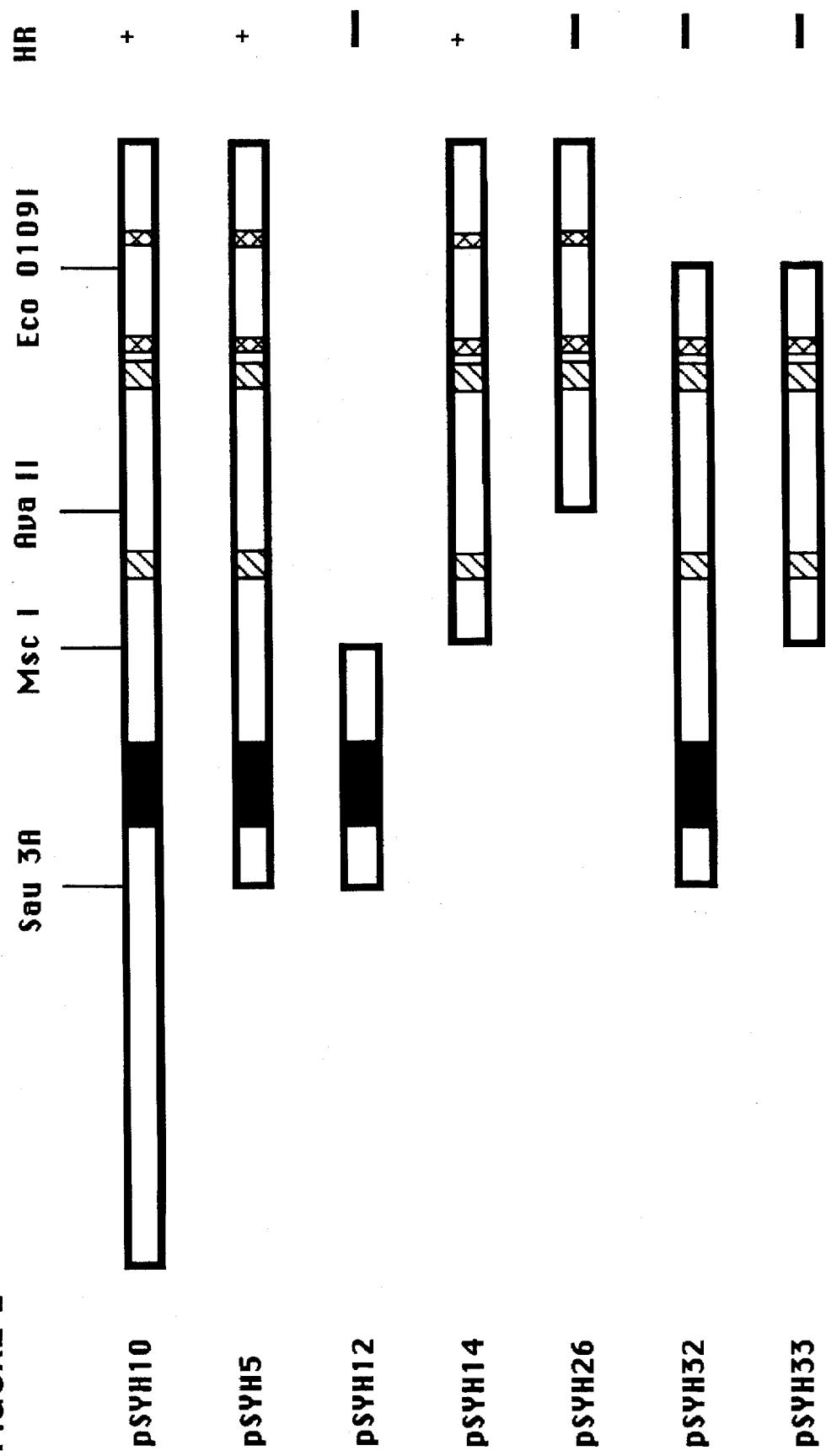
FIG. 2 depicts a diagram of the hrpZ fragments used to test the role of conserved or repeated amino acid sequences in the elicitor activity of Harpin$_{Pss}$ according to the present invention.

EXAMPLE IV pSYH12 [FIG. 2] was derived from pSYH5 by digestion with MscI and KpnI, treatment with T4 DNA polymerase, and religation. pSYH14 carries the 0.73 kb MscI-EcoRV fragment of pSYH5 in the EcoRV site of Bluescript SK(−); pSYH26 carries the T4 DNA polymerase-treated 0.6 kb AvaII-EcoRV fragment from pSYH5 in the EcoRV site of pBluescript; and pSYH32 carries the T4 DNA polymerase-treated 0.73 kb PvuII-EcoO1091 fragment of pSYH5 in the SmaI site of pBluescript SK(−). All constructs resulted in translational fusions with the amino-terminal 30 to 41 amino acids of β-galactosidase and translational terminations at either the hrpZ stop codon (pSYH14 and pSYH26) or the stop codons in the pBluescript SK(−) multiple cloning region (pSYH12, pSYH32, and pSYH33). Elicitor activity assays were initiated by growing *E. coli* DH5α transformants overnight at 30° C. in Terrific Broth and in the presence of 0.5 mM IPTG. Cells were collected by centrifugation, washed twice in 5 mM MES (pH 5.5), resuspended in one-fifth volume of the same buffer containing 1 mM PMSF, and disrupted by sonication. The sonicates were centrifuged at 16,500×g for 10 min. and the supernatant fraction was infiltrated into tobacco leaves.

As described, a screening procedure employing in planta bacterial lysis facilitated identification of *E. coli* transformants expressing a *P. syringae* HR elicitor according to the present invention. The ability of pHIR11 to confer HR-eliciting activity on nonpathogenic bacteria suggested to us that its hrp cluster may be carrying a gene encoding the elicitor, and thus an expression library of partially digested Sau3A fragments (1.5–3.5) of pHIR11 in pBluescript SK was prepared and *E coli* transformants was screened for HR-eliciting activity in tobacco leaves. Previous observations suggested that the use of an in situ lysis technique would facilitate detection of elicitor activity. Earlier reports had noted that the envA 1 mutation that confers outer membrane leakiness in *E. coli* MB5504 could not phenotypically suppress the hrpH mutation in pHIR11 [see J. Bacteriol. 174:6878 (1992)], which led us to believe that an elicitor produced by hrp subclones in the absence of other hrp genes might be cytoplasmic and therefore detectable only after cell lysis. Subsequent to the present invention, it had not been observed that any elicitor activity could be determined in culture fluids or sonictated extracts of *E. coli* MC4100 (ATCC deposit no. 35695)(pHIR11), *Pseudomo-* nas fluorescens 55(pHIR11), and Pseudomonas syringae pv syringae 61 (pHIR11) treated with 1 mM phenylmethylsulfonyl fluoride (PMSF, a serine protease inhibitor). This suggested to us that the elicitor might be quite labile.

To circumvent the preparation of lysates ex planta, we developed (Example I) one aspect of the present invention, a procedure for lysing E. coli cells in plants through treatment with EDTA and lysozyme at the time of inoculation. Two out of 200 randomly chosen E. coli transformants (1.0%) screened by this technique were found to produce the rapid leaf tissue collapse characteristic of the HR. Collapse did not occur when the lysis step was omitted, or when the lysis was performed on E. coli DH5α cells lacking these two subclones. Plasmids pSYH1 and pSYH4 were isolated from the two positive transformants.

Overlapping subclones produced harpin$_{Pss}$ and a truncated derivative, both of which possessed heat-stable, HR-eliciting activity. Restriction maps of pSYH1 and pSYH4 (FIG. 1) show that the inserts in the two plasmids overlapped in a 2.0-kb region that corresponded with complementation group XII of pHIR11. Interestingly, the two plasmids expressed proteins of different sizes as shown by SDS PAGE analysis; pSYH1 expressed a 32 kDa protein, and pSYH4 expressed a 42 kDa protein. Both proteins remained soluble and retained >85% of their elicitor activity after incubation at 100° C. for 10 min, which facilitated rapid, partial purification. Following purification to homogeneity by electrophoresis through 4.0% agarose, the proteins elicited the HR in tobacco leaves at 0.6 μM (32 kDa protein) and 2.4 μM (42 kDa protein). Further subcloning revealed that the 32 kDa protein was a truncated product of the 42 kDa protein. Thus, the truncated derivative was 4-times more potent than the full-length protein in eliciting the HR. Following convention, the name $harpin_{pss}$ has been used for the 42 kDa protein to distinguish it from the *Erwinia amylovora* harpin reported by Beer [see Science 257:85 (1992)] which we now refer to as $harpin_{Ea}$. The 32 kDa protein encoded by pSYH4 has an amino-terminal deletion of 125 amino acids and accordingly is referred to as $harpin_{pss}Δ125$. $Harpin_{pss}$ appears to be the only HR elicitor encoded by pHIR11; no other clones showed any HR-eliciting activity.

We have also shown herein that $harpin_{pss}$ is produced by *Pseudomonas syringae* pv syringae 61 in a minimal medium that derepresses hrp gene expression, and that the protein is secreted in a HrpH-dependent manner. To show this, antibodies were raised in rabbits against the 42 kDa $harpin_{pss}$ protein purified from *E. coli* DH5α(pSYH4), using conventional techniques, and used to probe immunoblotted SDS-PAGE gels loaded with the same protein and with proteins from *Pseudomonas syringae* pv syringae 61. The *Pseudomonas syringae* pv syringae 61 cultures were grown in either King's B medium or in hrp-derepressing minimal medium. Both cell lysate and culture fluid fractions were then analyzed. FIG. 4A shows that *Pseudomonas syringae* pv syringae 61 produced a protein that cross-reacted with the anti-$harpin_{Pss}$ antibodies and had the same mobility as the purified $harpin_{Pss}$. FIG. 4B shows that this protein was not produced by *Pseudomonas syringae* pv syringae 61 in King's medium, which represses hrp gene expression [see Science 245:1374 (1989); Appl. Environ. Microbiol. 55:1724 (1989); J. Bacteriol. 174:3499 (1992); and J. Bacteriol. 174:1734 (1992)]; nor was this protein produced by hrpZ mutant *Pseudomonas syringae* pv syringae 61-2092. The results confirm the production of the 42-kDa $harpin_{Pss}$ protein by wild-type *Pseudomonas syringae* pv syringae 61 and argue against any apparent hrp-dependent posttranslational processing of the protein.

To determine the localization of $harpin_{Pss}$ in *Pseudomonas syringae* pv syringae 61, cultures were grown for 24 hr in hrp-derepressing minimal medium, fractionated by centrifugation, and then analyzed for the distribution of $harpin_{Pss}$ by immunoblotting on SDS-PAGE gel and probing with anti-$harpin_{Pss}$ antibodies. As shown in FIG. 4B, more than half of the $harpin_{Pss}$ was found in the culture supernatant. Coomassie blue staining of the total protein in the culture supernatant and cell lysate demonstrated that the release of $harpin_{Pss}$ could not be attributed to cell lysis, as shown in FIG. 4C. Moreover, FIG. 4B shows that $harpin_{Pss}$ was not secreted to the medium of the hrpH mutant *Pseudomonas syringae* pv syringae 61-2089. hrpH encodes an envelope protein with sequence similarity to outer membrane proteins known to be involved in protein or phage secretion in several Gram-negative bacteria, and the protein is required for *Pseudomonas syringae* pv syringae 61 to elicit the HR. As predicted, $harpin_{Pss}$ was produced, but retained, in hrpH cells. Thus, $harpin_{Pss}$ is an extracellular protein secreted via the Hrp secretory pathway, and its transport is essential for elicitation of the HR.

The observation that $harpin_{Pss}$ was secreted suggested that the extracellular fluids of *Pseudomonas syringae* pv syringae cultures grown in hrp-depressing medium should possess elicitor activity, despite our previous failure to detect it. The dialyzed supernatant of a culture of *Pseudomonas syringae* pv syringae 61 was, indeed, found to elicit a typical HR in tobacco leaves, but only if heated to 100° C. for 10 immediately upon harvest, dialyzed in the presence of PMSF, and then concentrated >30-fold by ultrafiltration. Identically prepared supernatants from a culture of *Pseudomonas syringae* pv syringae 61-2089 failed to elicit HR.

The DNA sequence analysis of hrpZ according to the present invention revealed its product $harpin_{Pss}$ to be a glycine-rich protein with no extensive similarity to known proteins. The nucleotide sequences of the DNA inserts in pSYH10 and pSYH5 were determined using conventional techniques in the art, and are shown below in the DNA sequence of the hrpZ gene according to the present invention:

→ pSYH10
Sau3A
GATCCGGAAC TCGGTCGTCC AGTTCTGATT TCTTGACGCC CCTTCATACC 50
TGAGGGGGCT GCTACTTTTA GGAGGTTGTG 80

```
                                       -continued
ATG CAG AGT CTC AGT CTT AAC AGC AGC TCG CTG CAA ACC 119
CCG GCA ATG GCC CTT GTC CTG GTA CGT CCT GAA GCC GAG 158
ACG ACT GGC AGT ACG TCG AGC AAG GCG CTT CAG GAA GTT 197
GTC GTG AAG CTG GCC GAG GAA CTG ATG CGC AAT GGT CAA 236
                                        BstXI
CTC GAC GAC AGC TCG CCA TTG GGA AAA CTG TTG GCC AAG 275
TCG ATG GCC GCA GAT GGC AAG GCG GGC GGC GGT ATT GAG 314
GAT GTC ATC GCT GCG CTG GAC AAG CTG CAT GAA AAG 353
CTC GGT GAC AAC TTC GGC GCG TCT GCG GAC AGC GCC TCG 392
GGT ACC GGA CAG CAG GAC CTG ATG ACT CAG GTG CTC AAT 431
                        ——> pSYH5/12/32
            Sau3A
GGC CTG GCC AAG TCG ATG CTC GAT GAT CTT CTG ACC AAG 470
            ——> pSYH8, pSYH9
            HindIII
CAG GAT GGC GGG ACA AGC TTC TCC GAA GAC GAT ATG CCG 509
ATG CTG AAC AAG ATC GCG CAG TTC ATG GAT GAC AAT CCC 548
GCA CAG TTT CCC AAG CCG GAC TCG GGC TCC TCG GTG AAC 587
GAA CTC AAG GAA GAC AAC TTC CTT GAT GGC GAC GAA ACG 626
                                 ——> pSYH14/33
            MscI    (pSYH12)
GCT GCG TTC CGT TCG GCA CTC GAC ATC ATT GGC CAG CAA 665
CTG GGT AAT CAG CAG AGT GAC GCT GGC AGT CTG GCA GGG 704
ACG GGT GGA GGT CTG GGC ACT CCG AGC AGT TTT TCC AAC 743
AAC TCG TCC GTG ATG GGT GAT CCG CTG ATC GAC GCC AAT 782
     ——> pSYH26
      AvaII
ACC GGT CCC GGT GAC AGC GGC AAT ACC CGT GGT GAA GCG 821
GGG CAA CTG ATC GGC GAG CTT ATC GAC CGT GGC CTG CAA 860
TCG GTA TTG GCC GGT GGT GGA CTG GGC ACA CCC GTA AAC 899
ACC CCG CAG ACC GGT ACG TCG GCG AAT GGC GGA CAG TCC 938
GCT CAG GAT CTT GAT CAG TTG CTG GGC GGG TTG CTG CTC 977
 EcoO109I(pSYH32,pSYH33)
AAG GGC CTG GAG GCA ACG CTC AAG GAT GCC GGG CAA ACA 1016
                                             BstXI
GGC ACC GAC GTG CAG TCG AGC GCT GCG CAA ATC GCC ACC 1055
TTG CTG GTC AGT ACG CTG CTG CAA GGC ACC CGC AAT CAG 1094
GCT GCA GCC 1103
TGACCGACAA CCGCCTGACG GAGAACTCAC GTGACCATTT CCCACCTTGG 1153
TAATGTTAAA AGCATCTCGC CGGAACTCGG GCAGGATGTG CCACAGGGGC 1203
TCGTTTCAGA ACCGGCCCAG GCGGATGTCG ACATCTTCAC CGCTGCCACG 1253
CAGCCGGACG GCGTTTCAAG TGGAGCGCCG CTTTCCGAGC ATATCGCCAG 1303
CGCAATTTCC GGCGGTCTGG GCGAAACCGA AAAAATGTCT CAGCAAGCGA 1353
                                   EcoRV
TGCGGTCGAT GAAGAAAGCC TCCGGGACTG GAGACGCGCT GGATATC  1400
```

The DNA sequence of the *Pseudomonas syringae* pv syringae 61 DNA fragment that is carried in pSYH10 and contains the complete hrpZ open reading frame is shown above along with relevant restriction sites defining the limits of other subclones described herein. Plasmids denoted after arrows carry deletions 5' of the indicated restriction site; plasmids denoted within parentheses carry deletions 3' of the indicated restriction site.

The predicted amino-acid sequence of the product of this DNA's product harpin$_{pss}$ according to the present invention is:

```
Met Gln Ser Leu Ser Leu Asn Ser Ser Ser Leu Gln Thr Pro Ala
                 5                  10                  15
```

-continued

```
Met Ala Leu Val Leu Val Arg Pro Glu Ala Glu Thr Thr Gly Ser
                 20                  25                  30
Thr Ser Ser Lys Ala Leu Gln Glu Val Val Val Lys Leu Ala Glu
                 35                  40                  45
Glu Leu Met Arg Asn Gly Gln Leu Asp Asp Ser Ser Pro Leu Gly
                 50                  55                  60
Lys Leu Leu Ala Lys Ser Met Ala Ala Asp Gly Lys Ala Gly Gly
                 65                  70                  75
Gly Ile Glu Asp Val Ile Ala Ala Leu Asp Lys Leu Ile His Glu
                 80                  85                  90
Lys Leu Gly Asp Asn Phe Gly Ala Ser Ala Asp Ser Ala Ser Gly
                 95                 100                 105
Thr Gly Gln Gln Asp Leu Met Thr Gln Val Leu Asn Gly Leu Ala
                110                 115                 120
Lys Ser Met Leu Asp Asp Leu Leu Thr Lys Gln Asp Gly Gly Thr
                125                 130                 135
Ser Phe Ser Glu Asp Asp Met Pro Met Leu Asn Lys Ile Ala
                140                 145
```

-continued

| | | | | | | | | | | | |
|---|---|---|---|---|---|---|---|---|---|---|---|
| Gln | Phe | Met | Asp | Asp | Asp | Asn | Pro | Ala | Gln | Phe | Pro Lys Pro Asp |
| 150 | | | | | 155 | | | | | 160 | |
| Ser | Gly | Ser | Trp | Val | Asn | Glu | Leu | Lys | Glu | Asp | Asn Phe Leu Asp |
| 165 | | | | | 170 | | | | | 175 | |
| Gly | Asp | Glu | Thr | Ala | Ala | Phe | Arg | Ser | Ala | Leu | Asp Ile Ile Gly |
| 180 | | | | | 185 | | | | | 190 | |
| Gln | Gln | Leu | Gly | Asn | Gln | Gln | Ser | Asp | Ala | Gly | Ser Leu Ala Gly |
| 195 | | | | | 200 | | | | | 205 | |
| Thr | Gly | Gly | Gly | Leu | Gly | Thr | Pro | Ser | Ser | Phe | Ser Asn Asn Ser |
| | 210 | | | | 215 | | | | | 220 | |
| Ser | Val | Met | Gly | Asp | Pro | Leu | Ile | Asp | Ala | Asn | Thr Gly Pro Gly |
| 225 | | | | | 230 | | | | | 235 | |
| Asp | Ser | Gly | Asn | Thr | Arg | Gly | Glu | Ala | Gly | Gln | Leu Ile Gly Glu |
| 240 | | | | | 245 | | | | | 250 | |
| Leu | Ile | Asp | Arg | Gly | Leu | Gln | Ser | Val | Leu | Ala | Gly Gly Gly Leu |
| 255 | | | | | 260 | | | | | 265 | |
| Gly | Thr | Pro | Val | Asn | Thr | Pro | Gln | Thr | Gly | Thr | Ser Ala Asn Gly |
| | 270 | | | | 275 | | | | | 280 | |
| Gly | Gln | Ser | Ala | Gln | Asp | Leu | Asp | Gln | Leu | Leu | Gly Gly Leu Leu |
| 285 | | | | | 290 | | | | | 295 | |
| Leu | Lys | Gly | Leu | Glu | Ala | Thr | Leu | Lys | Asp | Ala | Gly Gln Thr Gly |
| 300 | | | | | 305 | | | | | 310 | |
| Thr | Asp | Val | Gln | Ser | Ser | Ala | Ala | Gln | Ile | Ala | Thr Leu Leu Val |
| 315 | | | | | 320 | | | | | 325 | |
| Ser | Thr | Leu | Leu | Gln | Gly | Thr | Arg | Asn | Gln | Ala | Ala Ala |
| | 330 | | | | 335 | | | | | 340 | |

In this amino acid sequence, the amino acids that were confirmed by sequencing of the purified harpin$_{Pss}$ are denoted in italics, the region of similarity with the *Erwinia amylovora* harpin$_{Ea}$ by a single underlined (identical amino acids are in bold), and repeated amino acid sequences within harpin$_{Pss}$ by double underlining.

The harpin$_{Pss}$ coding sequence starts at nucleotide 81, ends at 1103, and encodes a protein of 34.7 kDA. This is smaller than the size of harpin$_{Pss}$ estimated on SDS-PAGE gels (FIG. 3), and suggests that the protein might migrate abnormally in these gels. This was confirmed by a more accurate measurement of molecular mass using a mass spectrometer (Lasermat, Finngan Mat), which estimated harpin$_{Pss}$ to be 34.7 kDa and harpin$_{Pss}$Δ125 to be 25.1 kDa, in close agreement with the sequence predictions. Amino terminal sequencing of purified harpin$_{Pss}$ and harpin$_{Pss}$Δ125 confirmed the start codon of harpin$_{Pss}$ and revealed, as predicted by the sequence data, that harpin$_{Pss}$Δ125 has the N-terminal sequence of β-galactosidase, and is therefore a fusion protein.

Harpin$_{Pss}$ has no significant sequence similarity with sequences deposited in major sequence databases accessible with the Blast search program [see J. Mol. Biol. 215:403 (1990)]; nor were motifs of known biological significance detected for harpin$_{Pss}$ using the MOTIF program in the Genetics Computer Group Sequence Analysis Software Package [see Gene 12:387 (1984)]. However, an intriguing, albeit limited, sequence similarity was detected between harpin$_{Pss}$ and harpin$_{Ea}$ over a stretch of 22 amino acids. Harpin$_{Pss}$ is rich in glycine (13.5%) and lacks cysteine and tyrosine. The amino terminal sequence of harpin$_{Pss}$ is unlike typical sequences that would target proteins for translocation across the bacterial cytoplasmic membrane via the Sec export pathway. No obvious transmembrane, hydrophobic sequences are present in harpin$_{Pss}$. In fact harpin$_{Pss}$ appears to be highly hydrophilic and is a soluble cytoplasmic protein when expressed in *E. coli*. Because the gene encoding harpin$_{Pss}$ showed little relationship with the hrpN gene of *Erwinia amylovora* and encodes the apparent end product of the *P.s.syringae* 61 hrp cluster, it was designated hrpZ.

The carboxyl-terminal 148 amino acid portion of harpin$_{Pss}$ was found to contain two directly repeated sequences and is sufficient for elicitor activity. The two sequences, GGGLGTP and QTGT, are directly repeated in the portion of harpin$_{Pss}$ that is carboxyl-terminal to the 22 amino acid region showing similarity to harpin$_{Ea}$. To assess the importance of these features of harpin$_{Pss}$ in elicitor activity, a series of deletions were constructed in hrpZ. FIG. 2 depicts the hrpZ restriction sites that were exploited in the construction of subclones and deletion derivatives and the resulting truncated harpin$_{Pss}$ polypeptides. Immunoblot analysis with anti-harpin$_{Pss}$ antibodies confirmed the production of polypeptides of the predicted sizes by the various plasmids. *E. coli* DH5α cells carrying the plasmids were sonicated in the presence of PMSF, and soluble extracts were infiltrated into tobacco leaves. The differing effects of the polypeptides produced by pSYH14 demonstrated that the region of similarity with harpin$_{Ea}$ was neither sufficient nor necessary for elicitor activity. In contrast, a typical HR was elicited within 24 hr by all polypeptides carrying both of the repeated sequences. The effects of the polypeptides produced pSYH33 further suggest that both pairs of repeated sequences are essential for elicitor activity.

Southern Blot and Immunoblot analyses suggest that a hrpZ homolog is present and expressed in other *P. syringae* pathovars. To determine whether hrpZ sequences were present in other pathovars of *Pseudomonas syringae*, we used the BstXI fragment that is within hrpZ to probe a Southern blot of EcoR1-digested genomic DNA from *Pseudomonas syringae* pv syringae B728a, *Pseudomonas syringae* tomato DC3000, and *Pseudomonas syringae* glycinea race 4. These three strains were chosen because they represent diverse *Pseudomonas syringae* pathovars that are experimentally attractive. *Pseudomonas syringae* pv syringae B728a causes brown spot of bean and has become an acceptable model by plant pathologists for studying epiphytic fitness in *Pseudomonas syringae*; *Pseudomonas syringae* tomato DC3000 causes a bacterial speck of tomato and is also pathogenic on several ecotypes of *Arabidopsis thaliana;* and *Pseudomonas syringae* pv glycinea race 4 causes bacterial blight of soybean. The latter two strains are particularly useful for studying the phenomenon of avr gene-dependent (gene-for-gene) incompatibility. As seen in FIG. 5, a single band from each of these pathogens hybridized to the hrpZ probe, suggesting that the gene is widespread in *Pseudomonas syringae*. But the intensities of the hybridization signal varied, being strongest for *Pseudomonas syringae* pv syringae B728a, which is the strain most closely related to *Pseudomonas syringae* pv syringae 61. We also probed for the presence of hrpZ homolog in *X.c. glycines*, but observed no hybridization (FIG. 5, lane 5).

The production of proteins that cross-react with anti-harpin$_{Pss}$ was also assayed. Cells were grown in hrp-derepressing minimal medium for 24 hr and sonicated directly in the culture medium. The resultant lysates were analyzed by immunoblotting an SDS-PAGE gel. As shown in FIG. 6, cross-reacting bands were detected in all three strains of *Pseudomonas syringae*, but not in the nonpathogen *Pseudomonas fluorescens*.

Several higher plants, in addition to tobacco, were tested for their response to harpin$_{Pss}$, and different plants were found to exhibit different levels of sensitivity to harpin$_{Pss}$. These included two solanaceous plants (tomato and potato), two legumes (bean and soybean), and the model crucifer, *A. thaliana*. Harpin$_{Pss}$Δ125 and harpin$_{Pss}$ in 5 mM phosphate buffer (pH 6.5) elicited the HR in leaves of potato (>0.6 μM and >2.4 μM respectively) and tomato (>5 μM and >20 μM, respectively) within 7 to 16 hr, depending on the elicitor concentrations used. Harpin$_{Pss}$Δ125 also elicited the HR in leaves of soybean (>50 μM) and *A. thaliana* (>50 μM). No response was observed in leaves of bean (the host plant of Pseudomonas syringae pv syringae 61) at a concentration of 60 μM with either harpin$_{Pss}$Δ125 or harpin$_{Pss}$. Under the current assay conditions (without protease inhibitors) the HR in soybean and *A. thaliana* leaves were not observed consistently in response to harpin$_{Pss}$ and it varied from leaf to leaf. The different responses of different plants to harpin$_{Pss}$ may indicate that some plants such as soybean, *A. thaliana*, and bean have lower sensitivity to harpin$_{Pss}$ or degrade harpin$_{Pss}$ more rapidly, or both. It is important to note here that the response of these plant species to purified harpin$_{Pss}$ are correlated with their responses to harpin$_{Pss}$ producing bacteria, but that harpin$_{Pss}$ delivered by living bacteria appears to be more effective. For example, *Pseudomonas fluorescens* 55(pHIr11) elicited a visible HR in tobacco leaves at a lower cell density $1\times10^7$ cells/ml) than it did in *A. thaliana* leaves (>$1\times10^8$ cells/ml). At >$5\times10^8$ cells/ml, *Pseudomonas fluorescens* 55(pHIR11 ) weakly induced tissue necrosis in bean leaves.

The HR elicited by harpin$_{Pss}$ in tobacco was also found to be an active response of the plant. To see whether the HR induced by harpin$_{Pss}$ results from a directly toxic effect or from elicitation of an active response leading to necrosis, various inhibitors of plant metabolism were examined to determine if they could prevent the HR. Furthermore, the availability of purified harpin$_{Pss}$ enables inhibitors of plant metabolism to be used in the absence of possible interference with bacterial metabolism or hrp gene expression. The four inhibitors employed were α-amanitin (a specific inhibitor of eukaryotic RNA polymerase II), cycloheximide (a specific inhibitor of 80S ribosomes), vanadate (an inhibitor of ATPase and phosphatase), and lanthanum (a calcium channel blocker). All four inhibitors were found to effectively prevent the HR elicited harpin$_{Pss}$ in tobacco leaves when they were co-infiltrated with the purified protein at the concentrations of $2.2\times10^{-4}$M for α-amanitin, $7.1\times10^{-5}$M for cycloheximide, $5\times10^{-5}$M for vanadate, and $1\times10^{-3}$M for lanthanum. It is not known what concentrations of the inhibitors were inside plant cells during the experiment period (16–24 hr), nevertheless, the experiment clearly showed the harpin$_{Pss}$ elicited HR is an active process and may require the following important metabolic processes:de novo gene expression and protein synthesis, calcium flux across membranes, and ATPase activity. Thus harpin$_{Pss}$ acts as an elicitor of hypersensitivity, rather than as a directly toxic agent.

It has also been determined by the present invention that strong evidence exists indicating that Harpin$_{Pss}$ is the *Pseudomonas syringae* pv syringae 61 HR Elicitor.

We had previously observed that TnphoA insertions in all of the hrp complementation groups in the *Pseudomonas syringae* pv syringae 61 hrp cluster produce the null phenotype of a nonpathogenic bacterium [see Mol. Plant-Microbe Interact. 4:469 (1991)]. That is, the mutants fail to cause the HR in nonhost tobacco leaves to multiply or produce watersoaked, necrotic lesions in host bean leaves. On this basis, we postulated that the hrp genes are involved in the production of a single factor that is essential for *Pseudomonas syringae* pv syringae 61 to interact with plants. Several lines of evidence now indicate that harpin$_{Pss}$ is the active factor. First, harpin$_{Pss}$ is sufficient to elicit the HR in tobacco (the only phenotypic attribute that can be assayed in the absence of the bacterium); second, no other hrp genes in the expression library of pHIRII subclones possessed HR elicitor activity; third, harpin$_{Pss}$ is apparently essential for *Pseudomonas syringae* pv syringae 61 to elicit the HR in tobacco because mutations in complementation group XII (hrpZ) produce the typical null phenotype, whereas a residual effect on the plant would be expected if another elicitor were produced by the hrp cluster; fourth, an extracellular location for harpin$_{Pss}$ is consistent with its function as an elicitor and argues against an alternative role in the regulation or secretion of some other hrp product; and finally, harpin$_{Pss}$ is tightly regulated. This is consistent with the observation [see Science 245:1374 (1989)] that *Pseudomonas syringae* pv glycinea cells grown in minimal medium and treated with rifampicin upon inoculation can still elicit the HR, whereas cells grown in rich medium cannot do this. Additional characteristics predicted for the harpin are discussed below.

The finding that unrelated proteins of *Erwinia amylovora* and *Pseudomonas syringae* pv syringae elicit the HR suggests a working definition based on their common properties. Thus, harpins are hrp-encoded proteins that are hydrophilic, lack amino-terminal signal peptides, are heat stable, and elicit hypersensitive necrosis in many plants. Furthermore, we have shown here that harpin$_{Pss}$ is secreted into the bacterial medium via the Hrp secretory pathway, that the carboxyl-terminal 43% of the protein is sufficient for elicitor activity, and that the hypersensitivity of tobacco to harpin$_{Pss}$ is an active response of the plant.

Additional structural features of harpin$_{Pss}$ are noteworthy. First, the amino-acid composition of harpin$_{Pss}$ is generally similar to that of harpin$_{Ea}$. For example, both proteins are rich in glycine and lack cysteine. This suggests that the proteins have an open structure and is consistent with their resistance to denaturation by heat and their solubility in trichloracetic acid. Interestingly, the 148 amino acid product of pSYH14, which is the smallest polypeptide we constructed with elicitor activity, is particularly high in glycine (20%); second, the two harpins lack any stretches of hydrophobic amino acids that would serve as an inner membrane anchor; third, the two harpins carry an internal sequence in which 11 of 22 amino acids are identical (although this level of similarity does not reliably predict structural homology [see Genetics 9:56 (1991)], this region would be a candidate targeting signal for hrp-dependent translocation to the bacterial surface); fourth, two sequences, GGGLGTP and QTGT, are directly repeated in a carboxyl-terminal region of harpin$_{Pss}$ (although such repeated sequences are lacking harpin$_{Ea}$ they apparently are required for the elicitor activity of harpin$_{Pss}$; deletions affecting one member of either pair abolished elicitor activity (FIG. 2)); fifth, harpin$_{Pss}$ lacks tyrosine, and while it is tempting to speculate that this facilitates passage of the protein through the plant cell wall when $H_2O_2$-mediated cross-linking of tyrosine residue in cell wall proteins (a potential defense response) occurs, the lack of tyrosine residues is apparently not a universal characteristic of harpins, as harpin$_{Ea}$ has four [see Science 257:85 (1992)].

A fundamental question concerning the relationship between harpin$_{Pss}$ structure and function is whether the protein is an enzyme (with a substrate in the plant cell wall, for example) whose product is the actual elicitor, or whether the plant responds to information residing in the harpin structure itself; our hypothesis is that the latter is correct. For example, harpin$_{Pss}$ shows no pectolytic activity (pectic enzymes also can kill plant cells, but reports suggesting a role in elicitation of the HR have not been supported by subsequent genetic analysis), nor has any elicitor activity been found in protease-treated apoplastic fluids that have been recovered by centrifugation [see Physiol. Plant Pathol. 21:1 (1982)] from harpin$_{Pss}$-treated tobacco leaves. Furthermore, the heat stability of harpin$_{Pss}$ and the retention of activity in a truncated derivative lacking more than half of the native protein are properties that are uncharacteristic of enzymes.

The hrp clusters of *Pseudomonas syringae, Pseudomonas solanacearum, X. campestris* and *Erwinia amylovora* contain putative open reading frames for proteins similar to components of a secretion pathway in *Yersinia spp.* and other human pathogens [see Mol. Plant-Microbe Interact. 5:390 (1992); and Mol. Plant-Microbe Interact. 5:384 (1992) ]. The pathway is used by several extracellular, virulence ("Yop") proteins, all of which lack amino-terminal signal peptides and any other consensus targeting sequences [J. Bacteriol. 173:1677 (1991)]. The secretion of the Yop proteins to the medium and the virulence of *Yersinia spp.* are dependent on this pathway, which is encoded, at least in part, by a ysc (Yop secretion) operan. The similarities between the secretion pathway (components of these animal and plant pathogens has suggested that some of the hrp genes control the secretion of Yop-like proteins. Our finding that the *Pseudomonas syringae* pv syringae 61 HrpH protein (a YscC homolog) is required for harpin$_{Pss}$ secretion, provides direct experimental evidence for this hypothesis. The presence of YscC homologs in *Pseudomonas solanacearum* and *X. campestris* suggests that these bacteria also produce harpins. The likely universality of harpins among plant pathogenic bacteria that elicit the HR in nonhosts finds further experimental support in that *Pseudomonas solanacearum* produces one or more heat-stable, protease-sensitive factors that are secreted by Hrp+ cells and elicit HR-like necrosis in tobacco.

Despite the conservation of the hrp secretion genes, the genes encoding the harpins do not appear to be conserved among different genera of plant pathogenic bacteria. The lack of conservation is indicated by the dissimilarity of the *Erwinia amylovora* hrpN and *Pseudomonas syringae* pv syringae hrpZ genes and the failure of hrpZ to hybridize with the genomic DNA of *X. campestris*, a species whose diverse interactions with plants parallel those of *Pseudomonas syringae*.

Plant hypersensitivity to bacterial pathogens is generally considered to be an active response of the plant. Hypersensitive necrosis occurs many hours after inoculation, it does not require living bacteria once a relatively brief induction period has passed, and can be inhibited by darkness, high temperatures, protein synthesis, inhibitors such as blasticidin S, and calcium channel blockers such as cobalt and lanthanum. Although these treatments may have potentially confounding effects on bacterial metabolism and/or hrp gene expression, in toto, they strongly indicate that the *Pseudomonas syringae* HR elicitor acts in a nonhost as a signal that triggers a plant defense response pathway, rather than a toxic agent that directly kills plant cells. As described above, the necrosis elicited in tobacco leaves by harpin$_{Pss}$ does indeed require de novo transcription, translation, calcium influx, and ATPase activity. The similar effect on plants of living *Pseudomonas syringae* cells and isolated harpin$_{Pss}$ provides further evidence that *Pseudomonas syringae* elicits the HR solely through its production of extracellular harpin$_{Pss}$. An important implication of these findings is that gene expression events, specific transcripts, and routants blocked in the plant signal transduction pathway controlling hypersensitivity can now be pursued in the absence of bacteria, The uses to which the various aspects and portions of the present invention may be put to are many and varied. For example, hrpZ mutants may be used to identify, by complementation, genes from other plant pathogenic organisms (e.g., bacteria, fungi, nematodes) that encode proteins that function similarly to harpin. Although such proteins may have substantially different primary structures (and therefore would be difficult to detect by DNA hybridization techniques), these proteins should restore the ability to elicit the HR to either *Pseudomonas syringae* or *E. coli* cells carrying a hrp cluster that was functional, except for the hrpZ gene.

Another use within the scope of the present invention is to use harpin and/or harpin-producing strains to identify in plants harpin receptors and/or their interactants in signal transduction pathways and clone their encoding genes. Thus, this would allow one to exploit the potential of harpin to function (depending upon the plant) as a pathogenicity factor or as an elicitor of defense reactions to manipulate the structure or expression of plant genes (s) encoding harpin receptor(s) for the purpose of producing genetically engineered plants with improved resistance to plant pathogens.

Still another use of harpin within the scope of the present invention would be as a potentiator of secondary metabolite production in plants grown either naturally or in tissue culture.

Still another use would be the fusion of the gene encoding harpin to specific promoters of plant genes to develop specific transgenic plants. When the plant gene is "turned on", harpin would be expressed and the plant cell killed. Some appropriate plant gene promoters and their projected uses include genes involved in pollen development (resulting in the development of male sterile plants); genes that are expressed in response to infection by fungi, e.g. genes encoding phenylalanine ammonia lyase and chalcone synthase (the plant cell would be killed thereby limiting the progress of the fungus and making the plant resistant to fungal diseases); and genes involved in the development of senescence (to facilitate harvest, expression of hrp genes would result in defoliation).

Still another use of harpin within the scope of the present invention would be the use of harpin as a "target molecule" with which chemical compounds would be designed to react and thereby inactivate the bacterial harpin, which, because it is essential for disease, would provide a specific bacteriacide target.

Thus while we have illustrated and described the preferred embodiment of our invention, it is to be understood that this invention is capable of variation and modification, and we therefore do not wish to be limited to the precise terms set forth, but desire to avail ourselves of such changes and alternations which may be made for adapting the invention to various usages and conditions. Such variations and modifications, for example, would include the substitution of structurally similar sequences, for both the elicitor and hrpZ genes provided herein (whether derived from natural sources or synthetically manufactured), which function to yield substantially similar activities to those specifically described above. Thus, changes in sequence by the substitution, deletion, insertion or addition of nucleic acids (in the DNA sequences) or amino acids (in the peptide sequences) which do not substantially alter the function of those sequences specifically described above are deemed to be within the scope of the present invention. In addition, those fragments of the oligonucleotide sequence designated sequence No. 3 in the above sequence listing, i.e. the sequences shown as pSYH10, pSYH4, pSYH5, PSYH12, pSYH32, pSYH8, pSYH9, pSYH14, pSYH33, pSYH12, pSYH26, pSYH32 and pSYH33 are deemed to be within the scope of the present invention. Accordingly, such changes and alterations are properly intended to be within the full range of equivalents, and therefore within the purview of the following claims.

A listing of the nucleotide and amino acids described in the present application are as follows:

We claim:

1. An isolated *Pseudomonas syringae* protein capable of eliciting a hypersensitive response when said protein is introduced into tissue of a plant with which a *Pseudomonas syringae* pathogen is incompatible, under normal plant growth conditions, wherein the hypersensitive response is characterized by localized cell death in the plant tissue where the protein is introduced, the protein is glycine rich, lacks cysteine, is heat stable, lacks amino-terminal signal peptides, and is hydrophilic.

2. An isolated *Pseudomonas syringae* protein according to claim 1, wherein said protein comprises the amino acid sequence Gly Gly Gly Leu Gly Thr Pro.

3. An isolated *Pseudomonas syringae* protein according to claim 1, wherein said protein comprises the amino acid sequence Gln Thr Gly Thr.

4. An isolated protein according to claim 1, wherein the protein has a molecular weight of 34.7 kDa.

5. An isolated protein according to claim 4, wherein the protein has an amino acid sequence of SEQ. ID. No. 5.

6. An isolated protein according to claim 1, wherein the protein lacks tyrosine.

7. An isolated protein according to claim 1, wherein the protein has repeat amino acid sequences of SEQ. ID. Nos. 1 and 2.

8. An isolated protein according to claim 1, wherein the protein is purified.

9. An isolated protein according to claim 1, wherein the protein is recombinant.

10. An isolated protein fragment comprising a 25.1 carboxyl terminal fragment of the protein of claim 1.

11. An isolated protein fragment of the protein of claim 1 comprising amino acids 194 to 341 of SEQ ID NO:5.

* * * * *